US010241047B2

(12) United States Patent
Nuutinen et al.

(10) Patent No.: US 10,241,047 B2
(45) Date of Patent: *Mar. 26, 2019

(54) METHOD FOR ANALYSING A SAMPLE COMPRISING AT LEAST A FIRST AND A SECOND SCALE INHIBITOR

(71) Applicant: Kemira Oyj, Helsinki (FI)

(72) Inventors: Vesa Nuutinen, Helsinki (FI); Susanna Toivonen, Espoo (FI); James Johnstone, Banchory (GB); Harri Härmä, Turku (FI); Mirva Lehmusto, Turku (FI); Satu Tiittanen, Turku (FI); Pave Väisänen, Helsinki (FI); Joonas Siivonen, Turku (FI); Paul Mundill, Espoo (FI)

(73) Assignee: Kemira Oyj, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/716,616

(22) Filed: Sep. 27, 2017

(65) Prior Publication Data

US 2018/0017494 A1 Jan. 18, 2018

Related U.S. Application Data

(63) Continuation of application No. 15/037,682, filed as application No. PCT/FI2014/050878 on Nov. 18, 2014, now Pat. No. 9,816,927.

(30) Foreign Application Priority Data

Nov. 19, 2013 (FI) ..................................... 20136152

(51) Int. Cl.
*G01N 21/64* (2006.01)
*G01N 1/34* (2006.01)
*G01N 21/77* (2006.01)
*G01N 1/38* (2006.01)

(52) U.S. Cl.
CPC .......... *G01N 21/6408* (2013.01); *G01N 1/34* (2013.01); *G01N 1/38* (2013.01); *G01N 21/77* (2013.01); *G01N 2021/6419* (2013.01); *G01N 2021/6421* (2013.01); *G01N 2021/7786* (2013.01)

(58) Field of Classification Search
CPC .......... G01N 21/64; G01N 1/34; G01N 21/77; G01N 1/38
USPC .................. 436/104, 111, 129, 172
See application file for complete search history.

(56) References Cited

U.S. PATENT DOCUMENTS

| 3,962,110 | A | * | 6/1976 | Tate | .......................... | C02F 5/12 252/181 |
| 4,808,541 | A | * | 2/1989 | Mikola | .................. | C07F 9/3817 435/968 |
| 5,389,548 | A | * | 2/1995 | Hoots | .................. | G01N 21/643 436/6 |
| 5,418,614 | A | * | 5/1995 | Brost | .................. | G01N 21/8507 250/227.23 |
| 5,658,798 | A | * | 8/1997 | Bertin | ................ | G01N 21/6486 436/172 |
| 5,702,684 | A | * | 12/1997 | McCoy | .................... | A01N 61/00 210/745 |
| 6,312,644 | B1 | * | 11/2001 | Moriarty | ................ | C09K 11/06 252/180 |
| 6,329,205 | B1 | * | 12/2001 | Diwu | ....................... | G01N 1/30 436/172 |
| 6,344,360 | B1 | * | 2/2002 | Colvin | .................... | C07F 5/025 436/166 |
| 6,645,428 | B1 | * | 11/2003 | Morris | ....................... | C02F 5/12 252/301.35 |
| 6,790,664 | B2 | * | 9/2004 | Bailey | .................. | G01N 21/643 436/172 |
| 8,980,123 | B2 | * | 3/2015 | Moore | ....................... | C02F 5/12 252/180 |
| 9,816,927 | B2 | * | 11/2017 | Nuutinen | ........... | G01N 21/6408 |
| 9,902,904 | B2 | * | 2/2018 | Nuutinen | ................ | C09K 11/06 |
| 9,958,389 | B2 | * | 5/2018 | Nuutinen | ........... | G01N 21/6408 |
| 2002/0077262 | A1 | * | 6/2002 | Klein | ........................ | C08F 8/30 510/247 |
| 2003/0124730 | A1 | * | 7/2003 | Bailey | .................. | G01N 21/643 436/172 |
| 2004/0135124 | A1 | * | 7/2004 | Morris | ....................... | C02F 5/12 252/408.1 |

(Continued)

FOREIGN PATENT DOCUMENTS

| CN | 1811430 A | 8/2006 |
| CN | 101936874 A | 1/2011 |

OTHER PUBLICATIONS

Chinese Patent Office, Official Action of Chinese Patent Application No. 201480073518.6, dated Mar. 9, 2018.

*Primary Examiner* — Arlen Soderquist

(74) *Attorney, Agent, or Firm* — Berggren LLP

(57) ABSTRACT

The invention relates to a method for analysing a sample comprising at least a first and a second scale inhibitor, which scale inhibitors are synthetic organic compounds comprising at least one ionised group. The method comprises optionally diluting and/or purifying the sample, and allowing the sample interact with a reagent comprising lanthanide(III) ion. The sample is excited at a first excitation wavelength and a sample signal deriving from the lanthanide(III) ion is detected at a signal wavelength by using time-resolved luminescence measurement. The total concentration of the first and the second scale inhibitor is determined by using the detected sample signal, and the concentration of the first scale inhibitor in the sample is determined. The concentration of the second scale inhibitor is determined mathematically by using the obtained results for the total concentration and for the first scale inhibitor concentration.

15 Claims, 2 Drawing Sheets

(56) References Cited

U.S. PATENT DOCUMENTS

| | | | | |
|---|---|---|---|---|
| 2004/0135125 A1* | 7/2004 | Morris | C02F 5/12 | 252/408.1 |
| 2005/0036903 A1* | 2/2005 | Colclasure | G01N 33/1853 | 422/14 |
| 2005/0242042 A1* | 11/2005 | Moriarty | C02F 1/008 | 210/696 |
| 2007/0117215 A1* | 5/2007 | Davis | G01N 21/643 | 436/172 |
| 2007/0267193 A1* | 11/2007 | Hills | C02F 5/12 | 166/264 |
| 2008/0062417 A1* | 3/2008 | Stave | G01J 3/44 | 356/301 |
| 2008/0169243 A1* | 7/2008 | Dave | C02F 5/12 | 210/699 |
| 2008/0277083 A1* | 11/2008 | Shevchenko | D21C 3/226 | 162/48 |
| 2009/0101587 A1* | 4/2009 | Blokker | C02F 5/12 | 210/701 |
| 2010/0304418 A1* | 12/2010 | Moussavi | E21B 47/1015 | 435/28 |
| 2011/0027803 A1* | 2/2011 | Moussavi | C08F 2/005 | 435/7.9 |
| 2012/0032093 A1* | 2/2012 | Moore | C02F 5/12 | 250/459.1 |
| 2013/0234063 A1* | 9/2013 | Moore | C02F 5/12 | 252/180 |
| 2014/0060659 A1* | 3/2014 | Liang | G01N 21/6486 | 137/2 |
| 2014/0080172 A1* | 3/2014 | Tunheim | G01N 21/75 | 435/34 |
| 2014/0100142 A1* | 4/2014 | MacEwan | C02F 5/14 | 507/219 |
| 2014/0183140 A1* | 7/2014 | Atkins | C02F 5/12 | 210/701 |
| 2014/0186210 A1* | 7/2014 | Gill | C02F 5/125 | 422/3 |
| 2014/0260708 A1* | 9/2014 | Harrell | G01N 33/2823 | 73/866 |
| 2014/0298872 A1* | 10/2014 | Gill | C05G 3/00 | 71/27 |
| 2015/0184069 A1* | 7/2015 | Nuutinen | C09K 11/06 | 210/700 |
| 2016/0290923 A1* | 10/2016 | Nuutinen | G01N 21/6408 | |
| 2016/0290924 A1* | 10/2016 | Nuutinen | G01N 21/6408 | |
| 2017/0002629 A1* | 1/2017 | Hurtevent | C09K 8/528 | |

* cited by examiner

METHOD FOR ANALYSING A SAMPLE COMPRISING AT LEAST A FIRST AND A SECOND SCALE INHIBITOR

PRIORITY

This application is a continuation application of U.S. application Ser. No. 15/037,682 filed on May 19, 2016, and issued as U.S. Pat. No. 9,816,927 on Nov. 14, 2017 and claiming priority of the international application PCT/FI2014/050878 filed on Nov. 18, 2014 and claiming priority of Finnish national application FI20136152 filed on Nov. 19, 2013, the contents of all of which are incorporated herein by reference.

FIELD OF THE INVENTION

The present invention relates to a method for analysing a sample comprising at least a first and a second scale inhibitor according to the preambles of the enclosed independent claims.

BACKGROUND OF THE INVENTION

Scale inhibitors are used, for example, in offshore oil production for stimulation of the oil wells, for controlling and/or preventing scale depositions. A scale inhibitor may be injected continuously into an oil well, or it may be periodically injected if a so-called squeeze treatment is employed. In the squeeze treatment a scale inhibitor pulse is injected into the oil well and the scale inhibitor leaches back into the produced fluids. The concentration of the scale inhibitor in the produced fluids should be sufficiently high in order to avoid scale formation or precipitation. The concentration of scale inhibitor normally decreases exponentially after the initial injection, and when the concentration has fallen below a predetermined value the squeeze treatment of the oil well is repeated. Consequently, it is important to obtain reliable knowledge about the concentration of the scale inhibitor in the produced fluids for securing well-timed squeezing treatment. If the squeezing treatment is performed too late, harmful scales may be formed and disturb the production process.

Nowadays different analytical techniques are used for determining the scale inhibitor concentration in the produced fluids. Examples of used techniques are inductively coupled plasma (IPC), high-performance liquid chromatography (HPLC) and liquid chromatography-mass spectrometry (LC-MS). However, there is a continuous need for new, accurate and simple analysis methods.

Furthermore, in many oilfields a number of oil wells are squeezed at the same time. The produced fluids are a mixture of fluids from all the oil wells, and comprise scale inhibitor traces from each well. If different scale inhibitors are injected into each of the oil wells, it would be advantageous if the concentration of the different scale inhibitors could be determined separately. This would enable the correct individual squeeze treatment cycle for each oil well, separately from the other oil wells.

BRIEF DESCRIPTION OF THE INVENTION

It is an object of the present invention to reduce or even eliminate problems appearing in prior art.

An object of the invention is to provide a simple and reliable method for determining the concentrations of at least two scale inhibitors in a sample, especially in an oilfield sample.

Another object of the present invention is to provide a fast method for determining the concentrations of at least two scale inhibitors in a sample.

In order to realise the above-mentioned objects, among others, the invention is characterised by what is presented in the characterising parts of the enclosed independent claims.

Some preferred embodiments according to the invention are disclosed in the dependent claims presented further below.

Typical method according to the present invention for analysing a liquid sample comprising at least a first and a second scale inhibitor, which scale inhibitors are synthetic organic compounds comprising at least one ionised group, comprises optionally diluting and/or purifying the sample,
allowing the first and/or the second scale inhibitor in the sample interact with a reagent comprising lanthanide (III) ions,
exciting the sample at a first excitation wavelength and detecting a sample signal deriving from the lanthanide (III) ions at a signal wavelength by using time-resolved luminescence measurement,
determining the total concentration of the first and the second scale inhibitor by using the detected sample signal,
determining the concentration of the first scale inhibitor in the sample,
determining the concentration of the second scale inhibitor mathematically by using the obtained results for the total concentration and for the first scale inhibitor concentration.

The method according to the present invention is suitable for determining concentrations of scale inhibitors in any industrial water system or industrial water system samples where scale inhibitors are employed. These industrial water systems include, but are not limited to, cooling tower water systems, including open recirculating, closed and once-through systems; petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurisation water; water reclamation and purification systems; membrane filtration water systems; food processing streams, such as meat, vegetable, sugar beets, sugar cane, grain, poultry, fruit and soybean processing streams; and waste treatment systems as well as in clarifiers, liquid-solid applications, municipal sewage treatment and industrial or municipal water systems. Preferably the method is used for analysing scale inhibitor concentration from samples originating from petroleum wells, downhole formations, geothermal wells and other oil field applications. While some of the exemplary methods are described herein in relation to a sample originating from an oilfield or an oil well or from an oil production process, it will be understood that the methods may be adapted for use with other such samples and/or systems.

Now it has been surprisingly found out that by using the exemplary methods described herein the time-resolved luminescence signal derived from an interacted reagent comprising a lanthanide(III) ion, such as europium, excited at a suitable first wavelength, correlates accurately to the scale inhibitor concentration in a sample. This method may be utilised for determining the presence and/or concentration of a plurality of scale inhibitors in a sample, either individually or combined. According to the methods, the concentrations of the some individual scale inhibitors can be obtained by using time-resolved luminescence, while the concentrations of other scale inhibitors may be determined by other analytical technique or detection methods, e.g., direct fluorescent measurement, or may be determined indirectly, such as mathematical deduction. Thus according to the exemplary embodiments it is not necessary to directly determine the concentration of all individual scale inhibitors. The present invention also provides a method for detecting even low scale inhibitor concentrations in a sample, such as an oilfield sample. Significant reduction in the detection limit of scale inhibitor concentrations may be achieved by using time-resolved luminescence signal of a lanthanide(III) ion. The detected sample signal from the lanthanide(III) normally increases in the presence of scale inhibitors and correlates to the total concentration of the scale inhibitors in the sample. A further advantage is that the method according to the invention is simple and fast to perform.

As used herein the term "scale inhibitor" is used in its ordinary sense as understood by one skilled in the art, and thus may be used herein to refer to or describe synthetic chemical compositions or synthetic organic compounds, which comprise at least one ionised group, and which, when added to an aqueous system that tends to form scale, reduce, control, disperse or inhibit the formation, deposition and/or adherence of scale deposits on substrate surfaces in contact with a scale-forming aqueous system. In the context of the exemplary embodiments the term "scale inhibitor" denotes a synthetic organic compound or substance, preferably a synthetic polymer or copolymer.

As used herein the term "polymer" is used to denote a synthetic substance which is composed of a number of repeating monomer units, same or different, joined together to form a polymer backbone. A polymer is formed of at least two, preferably a plurality of monomers. As used herein the term "copolymer" is used to denote a polymer which comprises two or more different monomer units. The type of the copolymer depends on the arrangement of the different monomer units in its structure. The copolymer may be alternating, random, block or graft copolymer.

The sample, which comprises at least a first and a second scale inhibitors, is a liquid sample.

DETAILED DESCRIPTION OF THE INVENTION

Figure 1:
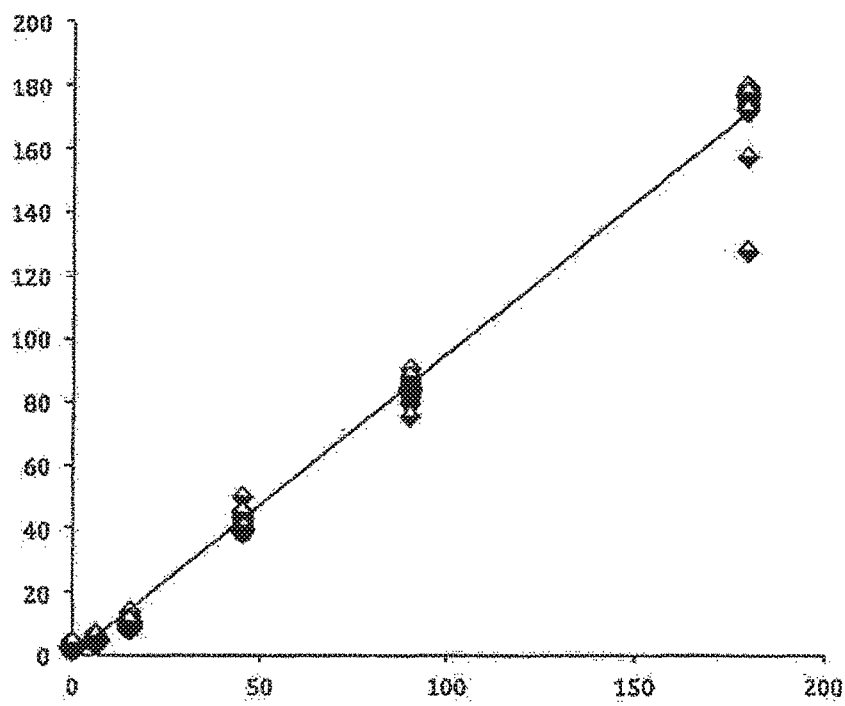
FIG. 1: Total concentration of scale inhibitor polymers.

According to one exemplary embodiment the first and/or the second scale inhibitors comprise at least one, preferably two or more ionised groups, more preferably at least three ionised groups, even more preferably at least four ionised groups, attached to the compound structure or polymer/copolymer backbone. According to another exemplary embodiment the scale inhibitors comprise one or two ionised groups, per at least some of the monomer units of the scale inhibitor polymer/copolymer. It is not necessary that all monomer units comprise ionised groups. The ionised groups may be selected from phosphates, phosphonates, carboxylates, sulphonates and/or amines, preferably from carboxylates, sulphonates and/or amines. Amines may be primary amines, secondary amines, tertiary amines and/or quaternary amines. Phosphates may be primary phosphates or secondary phosphates. In case the scale inhibitor comprises two or more ionised groups, the ionised groups in one scale inhibitor may all be similar to each other or they may be different from each other. A scale inhibitor may be anionic, cationic or zwitterionic, preferably anionic.

In exemplary embodiments one or more of the ionised groups of the scale inhibitor are capable of interacting with the reagents comprising lanthanide(III) ions. In this context the term "interact" means that the ionised groups can react, coordinate and/or chelate with the reagents comprising lanthanide(III) ions. Especially, the ionised groups of the scale inhibitor can react, coordinate and/or chelate with the lanthanide(III) ions.

According to various embodiments of the invention the scale inhibitors are selected from group comprising polyelectrolyte compounds comprising carboxylate and/or phosphonate groups; homopolymers and copolymers of ethylenically unsaturated acid monomers; organophosphonates; and combinations thereof. The polyelectrolyte compounds may comprise a multiplicity of interactive groups, which can be ionised, for example, carboxylate and/or phosphonate groups. The first and/or second scale inhibitor may be, for example, a polycarboxylic acid, such as polyacrylic acid, polymethacrylic acid, polymaleic acid or any of their salts with monovalent cations. Alternatively the first and/or second scale inhibitor may be, for example, maleic anhydride. The first and/or second scale inhibitor may be a homopolymer or a copolymer of an alpha, beta-ethylenically unsaturated acid monomer such as acrylic acid or methacrylic acid, a diacid such as maleic acid or maleic anhydride, itaconic acid, fumaric acid, monoesters of diacids with alkanols having 1-8 carbon atoms, and/or mixtures thereof. In case the first and/or second scale inhibitor is a copolymer, it may be composed of two or more co-monomers, and the first co-monomer may be any alpha, beta-ethylenically unsaturated monomer and the second co-monomer may be either a non-polar group or monomer, such as styrene or olefinic monomer; or a polar functional group or monomer, such as vinyl acetate, vinyl chloride, vinyl alcohol, an alkyl acrylate, vinyl pyridine, vinyl pyrrolidone, acrylamide or an acrylamide derivative, etc.; or an ionic functional group or monomer, such as styrenesulfonic acid, 2-acrylamido-2-methylpropanesulfonic acid (AMPS), vinylsulfonic acid, or vinylphosphonic acid. The first and/or second scale inhibitor may be an organophosphonate, such as amino tris(methylene phosphonic acid), 1-hydroxy ethylidene-1,1-diphosphonic acid, diethylenetriamine penta(methylene phosphonic acid) or phosphonobutane-tricarboxylic acid.

The scale inhibitor may have any necessary or desired molecular weight. For example, in an exemplary embodiment, the scale inhibitory may have a molecular weight of from about 500 to about 100 000 Daltons, preferably 500 to 100 000 Daltons, more preferably 500-30 000 Daltons, even more preferably 500-12 000 Daltons.

In exemplary embodiments, the dosing or concentration of the scale inhibitor(s) to an aqueous system will be an amount sufficient to produce a desired reduction, control, or inhibition result. In each system, the scale inhibitor(s) may have a predetermined set point, e.g. amount or range, to achieve a desired effect. The exemplary methods can be used to detect the concentration of the scale inhibitor(s) in the system, so that the predetermined effective amount(s) or range(s) can be achieved and/or maintained. For example, the total concentration of scale inhibitors in a liquid sample originating e.g. from an oilfield, oil well or from an oil production process, may be in the range of 0.5-200 ppm, preferably 1-50 ppm, more preferably 1-10 ppm. The sensitivity of the method may be selected so that it can detect the concentration of the scale inhibitors within the effective amount or range. For example, the method may be configured to directly detect or measure the concentration of the scale inhibitors in the liquid sample within this range. Alternatively, additional steps may be taken to adapt the method or modify the sample, e.g., with optional purification and/or dilution steps, so that the concentrations of the scale inhibitors therein fall within the detection limits of the method.

According to one embodiment of the invention, one or more of the scale inhibitors in a sample interact with a reagent comprising lanthanide(III) ion, and the resulting interaction product(s) is(are) detected using a time-resolved luminescence technique. An exemplary lanthanide(III) ion is selected from reagents comprising europium, terbium, samarium or dysprosium ions, preferably from europium or terbium ion. Even more preferably the lanthanide(III) ion is europium ion. Exemplary reagents comprising a lanthanide (III) ion may be a lanthanide(III) salt, such as $EuCl_3$ or $TbCl_3$, or a luminescent lanthanide chelate, such as {2,2', 2",2'''-[(4'-phenyl-2,2':6'-2"-terpyridine-6,6"-diyl)bis(methylenenitrilo)]tetrakis(acetato)}europium(III) or 2,2',2",2'''-[[4-[(4-phenyl)ethynyl]pyridine-2,6-diyl]bis(methylenenitrilo)]-tetrakis(acetato)europium(III).
Preferably, the reagent comprising a lanthanide(III) ion is a lanthanide(III) salt, such as $EuCl_3$ or $TbCl_3$, more preferably europium(III) salt, such as $EuCl_3$.

According to another embodiment of the invention it is also possible to use a combination of different reagents with same or different lanthanide(III) ions. For example, if the sample comprises a plurality of different scale inhibitors which have different affinity to different reagents and/or lanthanide(III) ions, it is possible to determine the total concentration of one or more of the scale inhibitors by using a sample signal from a first reagent having a lanthanide(III) ion and the concentration of one or more of the scale inhibitors by using a sample signal from a different second reagent having a lanthanide(III) ion.

According to an embodiment it is possible to use a relatively low amount of lanthanide(III) ion for determining the total scale inhibitor concentration in the sample. According to one embodiment the concentration of the lanthanide (III) ion may be in the range of 0.01-10 mM, preferably 0.01-1 mM, more preferably 0.01 mM-0.1 mM, even more preferably about 0.01 mM. The lanthanide(III) ion concentration is given for the final sample volume for which the time-resolved luminescence measurement is performed.

According to the various embodiments, time-resolved luminescence measurement can be used to measure the concentration of an individual scale inhibitor, or a plurality thereof, in a liquid sample, and/or to measure the combined concentration of a plurality of scale inhibitors. In embodiments in which an individual scale inhibitor concentration is being determined, the reagent comprising lanthanide(III) ion may be configured to preferentially interact with the selected individual scale inhibitor being measured, and the interaction product is detected using time-resolved luminescence measurement. In embodiments in which a combined concentration of a plurality of scale inhibitors is being determined, the reagent comprising lanthanide(III) ion may be configured to interact with all of the plurality of scale inhibitors, and the combined interaction products are detected using time-resolved luminescence measurement.

Preferably the time-resolved luminescence measurement is time-resolved fluorescence measurement. In time-resolved fluorescence, the sample containing the interaction product(s) of one or more scale inhibitor(s) and one or more reagent(s) comprising lanthanide(III) ion is excited at an excitation wavelength and the fluorescence sample signal is detected at an emission signal wavelength. An exemplary gate time between the excitation and emission may be, for example 0.5-800 µs, preferably 1-500 µs. The emission signal wavelength is typically longer than the excitation wavelength.

Excitation wavelengths, which are used in the present method, may be selected or determined by studying excitation maximums in the excitation spectra of the formed interaction products of each scale inhibitor and reagent(s) comprising lanthanide(III) ion. For example, the excitation wavelength may be in the range of 200-400 nm and the emission signal wavelength for the sample signal may be about 500-650 nm. For example, the excitation wavelength for europium is 340 nm and the optimum emission signal wavelength 615 nm. Correspondingly the excitation wavelength for terbium is 254 nm and the optimum emission signal wavelength 545 nm. The excitation spectrum for each respective interacted scale inhibitor and reagent comprising lanthanide(III) ion may be measured prior to starting the determination protocol or the excitation spectrum may be obtained or estimated from the literature.

For example, the second excitation wavelength may be substantially the excitation maximum of the first scale inhibitor in the presence of the reagent comprising lanthanide(III) ion, and a successive, third, excitation wavelength may be substantially the excitation maximum of the second scale inhibitor in the presence of the reagent comprising lanthanide(III) ion. The reagents for determining the first and the second scale inhibitor may be the same or different. The reagents may, for example, comprise different lanthanide(III) ions.

If time-resolved luminescence is being used to measure a plurality of interaction products within a sample, the method may be configured in order to better distinguish the interaction product signals from each other. For example, it is possible to use different excitation wavelengths, different reagents comprising different lanthanide(III) ions, and/or different signal modifiers, respectively, with one or more of the interaction products, to help to distinguish the signals resulting from such interaction products.

According to one embodiment it may be desirable to have a measurable difference between the excitation wavelengths of the first and second, and optionally any successive, interacted scale inhibitors. For example, the difference between the first excitation wavelength and the second excitation wavelength, and any successive excitation wavelength, may be at least 10 nm, preferably at least 20 nm, more preferably at least 25 nm. Depending on the sensitivity of the measurement device, a greater difference between the excitation wavelengths may make it easier to distinguish the detected signals corresponding to the respective scale inhibitor concentrations in the sample.

According to one embodiment of the invention a signal modifier, which comprises a metal ion, may be added to the sample before the excitation of the sample. The signal modifier may be used to modify the sample signal, e.g. its intensity, or to modify the difference between excitation wavelengths for different scale inhibitors. An exemplary signal modifier may comprise a metal ion, which is selected from a group comprising copper, nickel, chromium, iron, gold, silver, cobalt, and any of their mixtures. Preferably the signal modifier comprises copper(II). It may also possible to modify the effect of the sample matrix to the sample signal by using a signal modifier.

According to one embodiment of the invention the sample comprises three or more different scale inhibitors and the excitation is performed at three or more excitation wavelengths, respectively. Each excitation wavelength may be chosen according to the excitation maximum for each interacted scale inhibitor which is being determined.

According to one embodiment of the invention the concentration of the first scale inhibitor is determined by exciting the sample at a second excitation wavelength and detecting a first scale inhibitor signal by using time-resolved luminescence measurement. The first scale inhibitor signal may be detected at the signal wavelength or the first scale inhibitor signal may be detected at a first signal wavelength, which is different from the signal wavelength. It is also possible to determine the concentration of any successive scale inhibitor by exciting the sample at an individual successive excitation wavelength for each successive scale inhibitor or for each successive interaction product of each successive scale inhibitor and detecting successive scale inhibitor signal(s) by using time-resolved luminescence measurement. The successive scale inhibitor signals may be detected at suitable wavelengths, for example at a successive signal wavelength for each successive interacted scale inhibitor. At the first or successive wavelength may be excited one individual scale inhibitor or two or more scale inhibitors. In case two or more interaction products of two or more scale inhibitors are excited at the first or successive wavelength, the obtained signal correlates to the sum concentration of these excited scale inhibitors. Concentration of an individual scale inhibitor may be obtained mathematically by using the determined total concentration at the signal wavelength and one or more of the sum concentrations at the first or successive wavelengths.

The sample normally comprises at least two scale inhibitors, whose concentration in the sample is determined. The concentration of the individual scale inhibitors may be determined by using time-resolved luminescence or any other suitable analytical technique. According to one embodiment of the invention the concentration of the first, second and/or any successive scale inhibitor is determined by using luminescence, direct fluorescence, absorbance, spectrophotometry, optical rotation measurement, photon counting, inductively coupled plasma (IPC), high-performance liquid chromatography (HPLC), liquid chromatography-mass spectrometry (LC-MS), size exclusion chromatography, colorimetric methods, NMR, time-resolved luminescence, or a combination thereof. For determining individual concentrations for a plurality of different scale inhibitors, respectively, in one sample any possible combination of the said analytical techniques or detection methods may be used. For detecting a plurality of different scale inhibitors, respectively, in one sample any possible combination of the said analytical techniques or detection methods may be used. For example, in a sample comprising three scale inhibitors, the concentrations of the first and second scale inhibitors, as well as the total concentration, may be determined by using reagents comprising lanthanide(III) ions and time-resolved luminescence measurement and the concentration of the third scale inhibitor may be the determined mathematically by subtraction of the first and second scale inhibitor concentration from the total concentration.

Alternatively, one of the scale inhibitors may be tagged with a fluorescence tag, such as fluorescein, and the individual concentration of that tagged scale inhibitor may be determined with direct fluorescence detection of the tag.

In exemplary embodiments, the sample may be pretreated before the concentration of one or more scale inhibitors is measured. According to one embodiment of the invention the sample may be purified before the addition of and/or interaction with the reagent comprising lanthanide (III) ion for removal of disturbing or interfering substances and/or compounds. For example, pre-cleaning may help to minimize the background noise caused by the components of a liquid sample, e.g. water system. Exemplary purification methods include, e.g., centrifugation, size exclusion chromatography, cleaning with solid-phase extraction (SPE) cartridges, dialysis techniques, extraction methods for removing hydrocarbons, filtration, microfiltration, ultrafiltration, nanofiltration, membrane centrifugation, and/or other methods used to separate the polymeric species from smaller compounds, for example other treatment chemicals or salts. In an embodiment, salt concentration of the sample may be reduced or insoluble particles may be removed before addition of the reagent comprising lanthanide(III) ion and the time-resolved luminescence measurement. In another exemplary embodiment, if the initial concentration of the scale inhibitor in the sample is high, e.g. outside of the detection limits of the method, the sample may be diluted before addition and/or interaction with the reagent comprising lanthanide(III) ion. Possible diluents are water, one or more aqueous buffer solutions, or any of their mixtures. In exemplary embodiments, one or more of the above pretreatment steps may be performed on a sample before measurement of scale inhibitor concentration. For example, before measurement the sample may be either purified or diluted, or the sample may be both purified and diluted.

In exemplary embodiments, one or more buffers may be added to the sample prior to measurement, to improve the signal-to-noise and signal-to-background ratio of the detected sample signals. Examples of these buffers include, for example, those comprising sulfonic acid derivatives, such as e.g. HEPES (2-[4-(2-hydroxyethyl)piperazin-1-yl] ethanesulfonic acid, $pK_a$ 7.48), PIPES (1,4-piperazinediethanesulfonic acid, $pK_a$ 6.76), MOPS (3-morpholinopropane-1-sulfonic acid, $pK_a$ 7.2) and MES (2-(N-morpholino) ethanesulfonic acid, $pK_a$ 6.15), HEPES being preferred. Further, one preferred buffer is TRIS (2-Amino-2-hydroxymethyl-propane-1,3-diol), especially used as a mixture with a buffer comprising sulfonic acid derivative, such as HEPES.

According to one embodiment the pH value of the sample is adjusted to a suitable level, for example, in the range between pH 3 and pH 8, preferably in the range from pH 5 to pH 8. Any suitable buffer that does not significantly disturb the detection of the sample signal may be used. Exemplary buffers are given above, but other buffers may also be used.

The method according to the invention is quantitative, i.e. the signals which are obtained for the sample or for first, second or each successive scale inhibitor, correspond to the total concentration of all scale inhibitors or to the individual concentrations first, second or each successive scale inhibitor.

The analysis of the scale inhibitor concentrations according to the present invention may be performed in any suitable detection or fluid vessel. The fluid vessel may be e.g. a well, a part of a fluidic device, microfluidic chip or a cuvette. The fluid vessel may be selected to provide a predetermined amount of sample fluid for measurement. According to one embodiment of the invention the method may be performed in a single fluid vessel or in plurality of individual fluid vessels.

In case the concentration of the scale inhibitors are determined by using a plurality of fluid vessels, the determination of each may be performed separately, e.g., in parallel or series, by using suitable number of fluid vessels. For example, a predetermined number of fluid vessels may be selected, corresponding to the number of scale inhibitors to be detected. Each fluid vessel may be independently configured to determine a respective scale inhibitor. The same or different detection method may be used in each fluid vessel, depending for example on the nature of the scale inhibitor.

Each fluid vessel may independently comprise a selected suitable reagent for the scale inhibitor(s) to be determined in that vessel. The same or different analysis techniques may be used for different fluid vessels. For example, according to one embodiment of the invention the sample may comprise first, second and third scale inhibitor, of which the third scale inhibitor is tagged with a chromophore. A fixed volume of the sample is added to three fluid vessels. The first and second vessels comprise reagents with lanthanide(III) ions. In the first fluid vessel the scale inhibitors are allowed to interact with the reagent comprising lanthanide(III) ion, the sample is excited at the first excitation wavelength and the time-resolved fluorescence signal for the total scale inhibitor concentration is detected at the signal wavelength. In the second fluid vessel the first scale inhibitor is allowed to interact with the reagent comprising lanthanide(III) ion, the sample is excited at the second excitation wavelength, which is specific for the first scale inhibitor and the time-resolved fluorescence signal for the concentration of the first scale inhibitor is detected at the first signal wavelength. In the third fluid vessel the concentration of the third scale inhibitor is obtained by measurement of the inherent absorbance of the sample. Since only the third scale inhibitor comprises a chromophore, the measured absorbance is proportional to the concentration of the third scale inhibitor in the sample. In case the third scale inhibitor is tagged with a fluorescent tag, the determination of the concentration of the third scale inhibitor may be performed on basis of a direct fluorescence signal of the tag. Using the results obtained from the three fluid vessels, one may mathematically determine the respective concentrations of the first, second and third scale inhibitors in the sample, such by using an algorithm.

According to another embodiment of the invention the sample comprises a first scale inhibitor and a second scale inhibitor and the concentration of each in the sample is determined, respectively, in first and second fluid vessels. In the first fluid vessel, the first scale inhibitor is allowed to interact with a known amount of a reagent comprising terbium(III) ion. In the second vessel the second scale inhibitor is allowed to interact with a known amount of a reagent comprising europium(III) ion. The individual concentrations of the first and the second scale inhibitors are determined on basis of the measured time-resolved fluorescence sample signals of terbium and europium reacted with the first and second scale inhibitor, respectively.

According to one embodiment of the invention the method may be performed in a single fluid vessel. The sample comprises first, second and third scale inhibitor, of which the third scale inhibitor is tagged with a fluorophore. A fixed volume of the sample is added to a fluid vessel, e.g. cuvette, comprising a reagent comprising lanthanide(III) ion and the scale inhibitors are allowed to interact with the reagent comprising lanthanide(III) ion. The total concentration of the scale inhibitors in the sample is obtained when the sample is excited at the first excitation wavelength and the time-resolved fluorescence sample signal for the total concentration is detected at the signal wavelength. The concentration of the first scale inhibitor is obtained when the sample is excited at the second excitation wavelength, which is specific for the first scale inhibitor and the second time-resolved fluorescence sample signal is detected at the signal wavelength, this second sample signal corresponding to the concentration of the first scale inhibitor. The concentration of the third scale inhibitor is obtained by measurement of the specific fluorescence signal of the fluorophore.

The methods described herein may be automatized or they may be performed manually. According to an embodiment the method is performed as on-line measurement. In an exemplary embodiment, the measurement is preferably used on-site, such as at an offshore oil platform and provides almost instant information about on-going production. In some embodiments, the measurement time is relatively fast, so that for example the total measurement time for analysing one sample from optional purification to obtaining the scale inhibitor concentration value may be less than 15 minutes, preferably less than 10 minutes.

For determining the concentration of a scale inhibitor, a standard curve or standard point may be prepared before performing the determination method. The concentration of the scale inhibitor may be calculated on basis of the obtained sample signal by using the predetermined standard curve or the standard point. In corresponding manner a standard curve or standard point may be prepared for each successive scale inhibitor to be determined. Standard curve may also be prepared for the total concentration. Alternatively the measurement instrument may be pre-calibrated.

In case the sample comprises a plurality of scale inhibitors, which absorb excitation energy at the same wavelength, the sample signal may, in fact, correlate with the total concentration of all scale inhibitors in the sample.

The method according to one embodiment of the invention is suitable for analysing concentration of at least two scale inhibitors in a sample originating from an oilfield or an oil well or from an oil production process. For example, the invention is suitable for determining the concentration of at least a first and a second scale inhibitor in a sample, which is a mixture of fluids originating from at least two squeezed oil wells. The squeeze treatment cycle for each oil well is determined according to the obtained concentration results.

EXPERIMENTAL

An embodiment of the invention is described more closely in the following non-limiting example.

Example 1 employs scale inhibitor polymers, which are sulphonated polycarboxylates, i.e. copolymers comprising allylsulphonate- and maleic anhydride based monomers in 50/50 molar ratio. The molecular weight of the copolymers is between 1500 and 12 000 Da. In Example 1 the following scale inhibitor polymers, given in Table 1, are referenced:

TABLE 1

Scale inhibitor polymers of Example 1

| Polymer | Description |
|---------|-------------|
| P1 | Sulphonated polycarboxylate |
| P2 | Sulphonated polycarboxylate with a fluorescent moiety |
| P40 | Sulphonated polycarboxylate with a phosphorous moiety |

Example 1

Total concentration of a mixture of scale inhibitor polymers P1, P2 and P40 was measured by adding to a fluid vessel 400 µL of polymer in synthetic brine comprising 600 mM NaCl, 7 mM $MgCl_2*6H_2O$, 15 mM $CaCl_2*2H_2O$, 3 mM KCl and 0.5 mM $BaCl_2$ in MilliQ water solution. Thereafter, 100 µL of a solution containing 0.5 M $CaCl_2$, 1.25 mM tris(hydroxymethyl)aminomethane (TRIS), 12.5 mM of 2-[4-(2-hydroxy-ethyl)piperazin-1-yl]ethanesulfonic acid (HEPES), 8.3 µM bovine serum albumin and 0.8 µM of {2,2',2'',2'''-[(4'-phenyl-2,2':6'-2''-terpyridine-6,6''diyl)bis-(methylenenitrilo)]tetrakis(acetato)}europium(III) was added. 450 µL of the above-prepared solution was added to a 50 µL solution of 1.5 mM of $CuCl_2$ in water. 100 µL of this final solution was measured for time-resolved luminescence signal in a microtiter plate with the Victor 1420 luminescence reader using excitation wavelength of 340 nm, emission wavelength of 614 nm, delay time of 400 µs and measurement window 400 µs.

Then 250 µL of sample in synthetic brine containing the mixture of scale inhibitor polymers P1, P2 and P40 was additionally measured for fluorescence in a microtiter plate with a Tecan luminescence reader using excitation wavelength of 230 nm and a ratio of emission wavelengths of 290/320 nm, This non-gated fluorescence measurement using the wavelength selection resulted in the concentration of polymer P2.

Finally, 250 µL of sample in synthetic brine containing a mixture of scale inhibitor polymers P1, P2 and P40, 10 µM $EuCl_3$ and 5 mM HEPES-NaOH pH 7 was measured using the time-resolved luminescence with the Victor 1420 reader. Scale inhibitor polymer P40 yielded high luminescence signal levels compared to scale inhibitor polymers P1 and P2 providing a method to measure P40 concentration.

Figure 2:
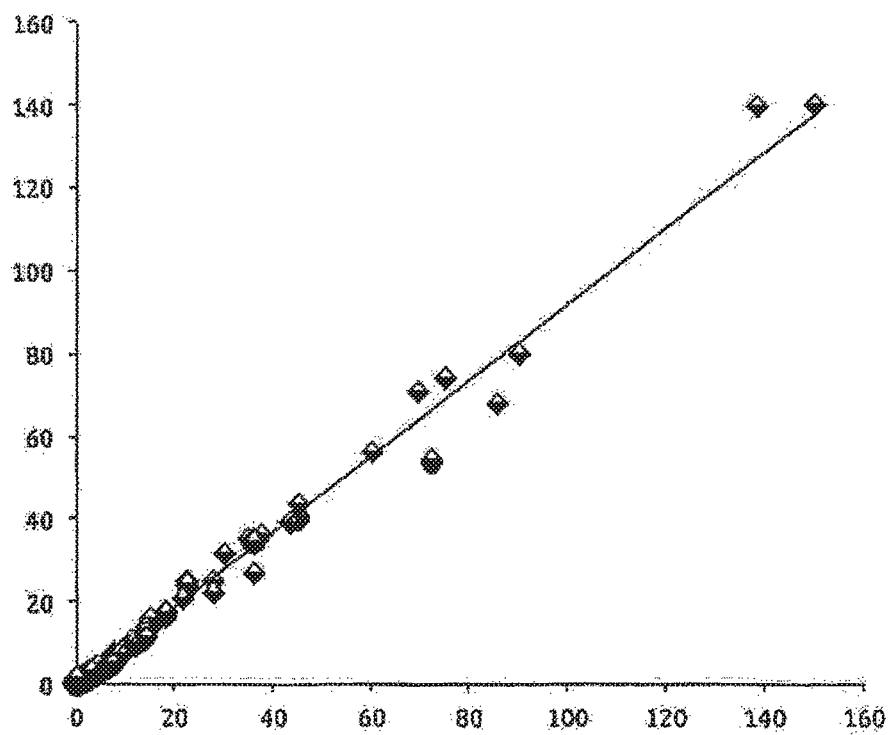
FIG. 2: Concentration of scale inhibitor polymer P2.
Figure 3:
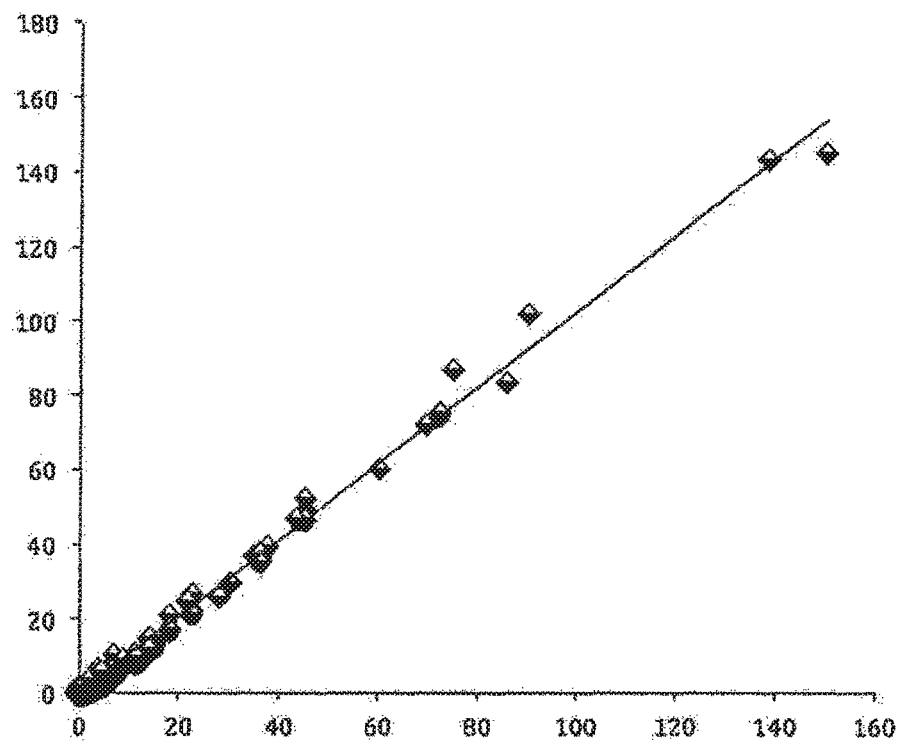
FIG. 3: Concentration of scale inhibitor polymer P40.
Figure 4:
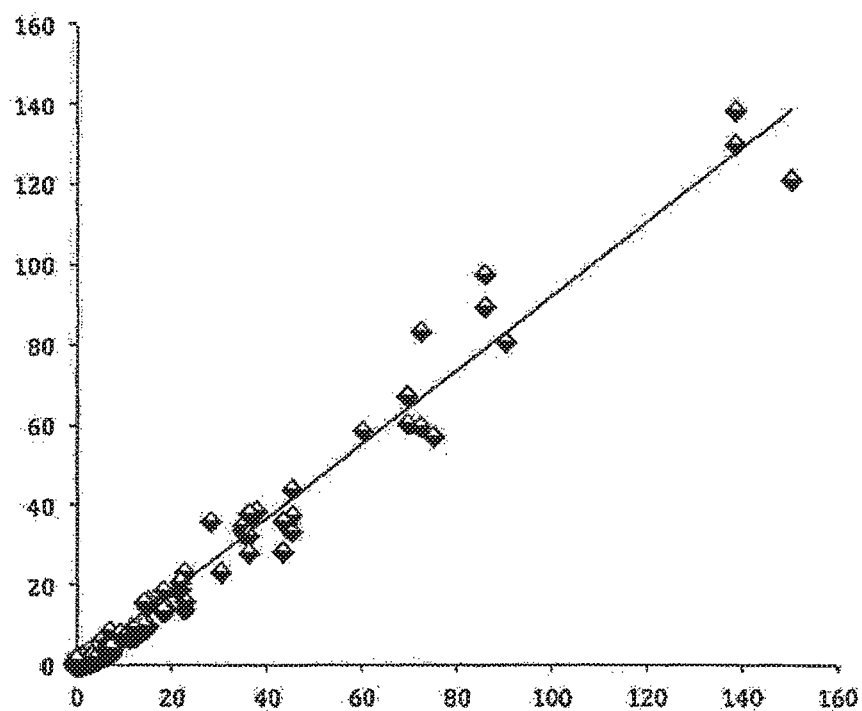
FIG. 4: Concentration of scale inhibitor polymer P1.

Consequently, the first measurement provided the total concentration of scale inhibitor polymers as shown in FIG. 1, the second measurement gave the concentration of scale inhibitor polymer P2 as shown in FIG. 2, the third measurement resulted in the concentration of scale inhibitor polymer P40 as shown in FIG. 3 and an algorithm was used to calculate from the obtained concentration data the concentration of scale inhibitor polymer P1 as shown in FIG. 4. Feed-forward neural network algorithm may be taught to calculate concentration of each scale inhibitor polymer using the information about concentrations of total polymers and polymers P2 and P40. In the FIGS. 1 to 4 X-axis denotes the actual polymer concentration in ppm, Y-axis denotes the measured polymer concentration in ppm.

It is apparent to a person skilled in the art that the invention is not limited exclusively to the examples described above, but that the invention can vary within the scope of the claims presented below.

The invention claimed is:

1. Method for analysing a sample comprising at least a first and a second scale inhibitor, which scale inhibitors are synthetic organic compounds comprising at least one ionised group, and determining concentrations of the scale inhibitors in an industrial water system, the method comprising
optionally diluting and/or purifying the sample,
allowing the sample interact with a reagent comprising lanthanide(III) ion,
exciting the sample at a first excitation wavelength and detecting a sample signal deriving from the lanthanide (III) ion at a signal wavelength by using time-resolved luminescence measurement,
determining the total concentration of the first and the second scale inhibitor by using the detected sample signal,
determining the concentration of the first scale inhibitor in the sample,
determining the concentration of the second scale inhibitor mathematically by using the obtained results for the total concentration and for the first scale inhibitor concentration.

2. Method according to claim 1, wherein the concentration of the first scale inhibitor is determined by exciting the sample at a second excitation wavelength and detecting a first scale inhibitor signal by using time-resolved luminescence measurement.

3. Method according to claim 2, wherein the first scale inhibitor signal is detected at the signal wavelength or a first signal wavelength, which is different from the signal wavelength wherein the difference between the first excitation wavelength and second excitation wavelength, and any successive excitation wavelength, is preferably at least 10 nm, more preferably at least 20 nm, even more preferably at least 25 nm.

4. Method according to claim 1, wherein the time-resolved luminescence measurement is time-resolved fluorescence measurement.

5. Method according to claim 1, wherein the concentration of the first, second and/or any successive scale inhibitor is determined by using luminescence, direct fluorescence, absorbance, spectrophotometry, optical rotation measurement, photon counting, inductively coupled plasma (IPC), high-performance liquid chromatography (HPLC), liquid chromatography-mass spectrometry (LC-MS), size exclusion chromatography, colorimetric methods, NMR, time-resolved luminescence, or a combination thereof.

6. Method according to claim 1, wherein the reagent comprising lanthanide(III) ion is a lanthanide(III) salt or a luminescent lanthanide chelate.

7. Method according to claim 1 wherein the lanthanide (III) ion is selected from reagents comprising europium, terbium, samarium or dysprosium ions, preferably from europium or terbium ions.

8. Method according to claim 1, wherein the concentration of the lanthanide(III) ion is in the range of 0.01-10 mM, preferably 0.01-1 mM, more preferably 0.01 mM -0.1 mM, even more preferably about 0.01 mM.

9. Method according to claim 1, wherein the first and/or second scale inhibitors comprise two or more ionised groups, which are selected from phosphates, phosphonates, carboxylates, sulphonates, and/or amines, preferably from carboxylates, sulphonates and/or amines.

10. Method according to claim 9, wherein the scale inhibitors are selected from group comprising polyelectrolyte compounds comprising carboxylate and/or phosphonate groups; homopolymers and copolymers of ethylenically unsaturated acid monomers; organophosphonates, and combinations thereof.

11. Method according to claim 1, wherein the industrial water system is selected from a group consisting of
cooling tower water systems;
boilers and boiler water systems;
mineral process waters;
paper mill digesters, washers, bleach plants and white water systems;
black liquor evaporators in the pulp industry;
gas scrubbers and air washers;
continuous casting processes in the metallurgical industry;
air conditioning and refrigeration systems;
indirect contact cooling and heating water;
water reclamation and purification systems;

membrane filtration water systems;
food processing streams; and
waste treatment systems.

12. Method according to claim 1, wherein the method is performed as on-line measurement.

13. Method according to claim 1, wherein the scale inhibitor is anionic.

14. Method according to claim 1, wherein the first and/or second scale inhibitor is a polycarboxylic acid selected from polyacrylic acid, polymethacrylic acid, polymaleic acid or any of their salts with monovalent cations.

15. Method according to claim 1, wherein the scale inhibitor has a molecular weight of from 500 to 100 000 Daltons, more preferably 500-30 000 Daltons, even more preferably 500-12 000 Daltons.

* * * * *